US007235693B2

(12) United States Patent
Buschmann et al.

(10) Patent No.: US 7,235,693 B2
(45) Date of Patent: Jun. 26, 2007

(54) PROCESS FOR CHLORINATING TERTIARY ALCOHOLS

(75) Inventors: Helmut Buschmann, Esplugues de Llobregat (DE); Wolfgang Hell, Aachen (DE); Markus Kegel, Aachen (DE)

(73) Assignee: Gruenenthal GmbH, Aachen (DE)

( * ) Notice: Subject to any disclaimer, the term of this patent is extended or adjusted under 35 U.S.C. 154(b) by 131 days.

(21) Appl. No.: 10/972,773

(22) Filed: Oct. 26, 2004

(65) Prior Publication Data
US 2005/0119349 A1 Jun. 2, 2005

Related U.S. Application Data

(63) Continuation of application No. PCT/EP03/04213, filed on Apr. 23, 2003.

(30) Foreign Application Priority Data
Apr. 26, 2002 (DE) ................ 102 18 862

(51) Int. Cl.
C07C 211/00 (2006.01)
(52) U.S. Cl. .................................... 564/338
(58) Field of Classification Search ................ 564/338
See application file for complete search history.

(56) References Cited
FOREIGN PATENT DOCUMENTS

| DE | 199 41 062 A1 | 3/2001 |
| EP | 0 831 082 A1 | 3/1998 |
| EP | 0 753 506 B1 | 8/1999 |
| GB | 2 182 039 A | 5/1987 |

OTHER PUBLICATIONS

International Search Report, 2003.
*Organikum, Organisch-chemisches Grundpraktikum*, 1988, pp. 188-191, VEB Deutscher Verlag der Wissenschaften, Berlin, Germany.
Fujii et al., "Regioselective Cleavage of Aromatic Methyl Ethers by Methanesulphonic Acid in the Presence of Methionine," *J.C.S. Perkin I*, 1977, pp. 2288-2289.
Irie et al., "Role of Methionine in the Facilitated Cleavage of Aromatic Ethers by Methanesulphonic Acid," *J.C.S. Chem. Comm.*, 1976, pp. 922-923.
AN: 1967:421507 HCAPLUS; NL 6610022; Abstract Only.
AN: 2001:685673 HCAPLUS, CN 1281850; Abstract Only.
International Preliminary Examination Report of corresponding International Application No. PCT/EP03/04213 dated Oct. 31, 2003.

*Primary Examiner*—Samuel Barts
(74) *Attorney, Agent, or Firm*—Crowell & Moring LLP

(57) ABSTRACT

The present invention relates to a process for converting a tertiary OH group of an organic compound into a tertiary Cl group of the organic compound by using a solvent selected from the group comprising toluene, o-xylene, m-xylene, p-xylene and mixtures thereof, and thionyl chloride as the chlorinating agent.

23 Claims, No Drawings

PROCESS FOR CHLORINATING TERTIARY ALCOHOLS

CROSS REFERENCE TO RELATED APPLICATIONS

This application is a continuation of international patent application no. PCT/EP03/04213, filed Apr. 23, 2003, designating the United States of America, and published in German as WO 03/091199 A1, the entire disclosure of which is incorporated herein by reference. Priority is claimed based on German patent application no. 102 18 862.9, filed Apr. 26, 2002.

FIELD OF THE INVENTION

The present invention relates to a process for converting a tertiary OH group of an organic compound into a tertiary Cl group of the organic compound.

BACKGROUND OF THE INVENTION

As is known from EP 0 753 506 A1, the compound of formula (I) (below) has an analgesic effect and is also used as an intermediate product to produce further analgesic substances. EP 0 753 506 A1 discloses a process for producing the compound of formula (I) starting from a compound of general formula (II),

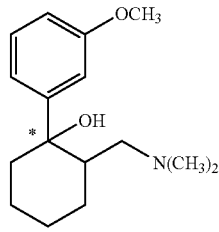

II the production of which is known from the literature (K. Flick et al., Arzneim.-Forsch./Drug Res. 28 (1), issue 1a (1978)), wherein, to convert the tertiary alcohol function on the cyclohexyl radical into a C-substitution with retention on the carbon atom marked by *, thionyl chloride is used as the chlorination reagent and as the solvent. This process therefore requires large quantities of thionyl chloride. The subsequent working up while expelling the excess thionyl chloride with a stream of nitrogen gas or by distillation is stressful for humans, the environment and operating equipment. Furthermore, only poor yields (maximum of 55% of theoretical) are achieved.

SUMMARY OF THE INVENTION

In particular the invention relates to a process for producing a compound of general formula (I)

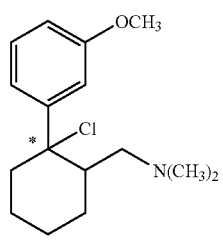

I and, more precisely, in the form of its racemates, its pure stereoisomers, in particular enantiomers or diastereomers, or in the form of mixtures of stereoisomers, in particular the enantiomers or diastereomers, in any mixing ratio; in the illustrated form or in the form of its salts, in particular the physiologically acceptable salts, particularly preferably in the form of the hydrochloride, or in the form of its solvates, in particular the hydrates.

It is therefore an object of the invention to provide a process with which an organic compound comprising a tertiary OH group, in particular a compound of formula (II), is converted into a corresponding organic compound comprising a tertiary Cl group, in particular into a compound of formula (I), in a high yield. It is also desirable to reduce the quantity of chlorinating agent to be used, compared to the process known from the literature, using this process.

The object is achieved by a process for converting a tertiary OH group of an organic compound into a tertiary Cl group of the organic compound, characterized in that the tertiary alcohol is suspended or dissolved in a solvent, selected from the group comprising toluene, o-xylene, m-xylene, p-xylene and mixtures thereof, thionyl chloride being added to the resultant suspension or solution and then the resultant organic compound comprising the tertiary Cl group is separated from the further reaction components.

It is preferred in this case that at least 1 equivalent but not more than 3 equivalents of thionyl chloride is/are used. The preferred solvent is toluene.

Separation of the resultant organic compound comprising the tertiary Cl group can be effected in different ways. Thus, the organic compound comprising the tertiary Cl group can be isolated, after the reaction has taken place, by distilling off (distillation of) the further reaction components with the solvent. Distilling off (distillation of) is also taken to mean the partial removal of the solvent with the further reaction components by supplying heat under vacuum. It is also possible, after the reaction has taken place, to obtain the organic compound comprising the tertiary Cl group as a solid by cooling to below ambient temperature and to then dry it at temperatures between 35° C. and 75° C., preferably under vacuum. The halogenated organic compound is preferably obtained in the form of its hydrochloride.

This process according to the invention allows synthesis of organic compounds comprising a tertiary Cl group, starting from the corresponding tertiary alcohol while retaining the stereochemistry at the stereogenic center in high yields of more than 70% and while reducing the quantity of thionyl chloride to be used.

The process according to the invention has proven to be particularly advantageous for producing a compound of formula (I)

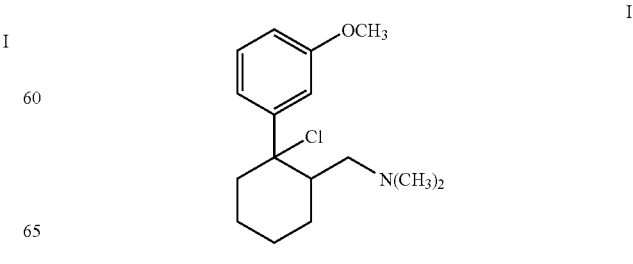

I in the form of its racemates, its pure stereoisomers, in particular enantiomers or diastereomers, or in the form of mixtures of stereoisomers, in particular the enantiomers or diastereomers, in any mixing ratio; in the illustrated form or in the form of its salts, in particular physiologically acceptable salts, particularly preferably in the form of the hydrochloride, and/or in the form of its solvates, in particular the hydrates; wherein the process is characterized in that a compound of formula (II)

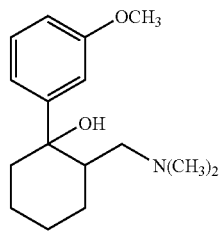

in the form of its racemates, its pure stereoisomers, in particular enantiomers or diastereomers, or in the form of mixtures of stereoisomers, in particular the enantiomers or diastereomers, in any mixing ratio; in the illustrated form or in the form of its salts, in particular physiologically acceptable salts, particularly preferably in the form of the hydrochloride, and/or in the form of its solvates, in particular the hydrates;

(a) is suspended in a solvent, which is selected from the group comprising toluene, o-xylene, m-xylene, p-xylene and mixtures thereof;
(b) thionyl chloride is added to the resultant suspension; and
(c) the reaction product comprising the tertiary Cl group of formula (I) is separated from the further reaction components.

It is advantageous here that the reaction product of formula (1) is separated (c) by distilling off (distillation of) the solvent with the further reaction components. Distilling off (distillation) includes, without limitation, the partial removal of the solvent with the further reaction components by supplying heat under vacuum. Alternatively, separation (c) can take place by precipitating the reaction product of formula (I) by means of cooling the reaction mixture to below ambient temperature and then drying the reaction product at temperatures between 35° C. and 75° C., preferably under vacuum.

Toluene is preferred as the solvent or solubilizer. The use of other non-polar solvents as toluene and/or xylene, for example THF, heptane, hexane and cyclohexane, has not proven to be advantageous, as the reaction is then carried out with the formation of numerous by-products, i.e. not sufficiently selectively. It is also preferred that 1 to 2 equivalents, in particular 1.5 to 1.7 equivalents, particularly preferably 1.6 equivalents of thionyl chloride—based on the compound of formula (II)—are used. This represents a drastic reduction in the quantity of thionyl chloride to be used compared with the process known from EP 0 753 506 A1. Much higher yields, which are greater than 70% of the theoretical yield, are also achieved with complete conversion of the starting compound (II).

The compound (II) is preferably reacted at elevated temperature, in particular at a temperature of 30 to 50° C., preferably 35 to 45° C., for 1 to 4 hours, preferably 2 to 3 hours, though the reaction time can also be longer or shorter than this.

It has been found that the reaction according to the invention of (II) to (I) in the presence of catalysts, for example dimethyl formamide, does not result in higher conversion rates or improved yields; however, these catalysts do not disturb the course of the reaction either.

The starting compound (II) is generally used in the form of its hydrochloride. It is suspended in the inert or non-polar solubilizer, toluene, in which it does not dissolve at either low or high temperature. The addition of the thionyl chloride, which for its part is relatively non-polar, should not make any difference but during the course of the reaction it will be seen that the educt (II) dissolves completely. It is also surprising, and advantageous to process management as a whole, that—in contrast to what is conventional in reactions with thionyl chloride, such as in the process of EP 0 753 506 A1 known from the literature, no sulphur dioxide gas and no hydrogen chloride gas develops during heating. It is possible that the educt of formula (II) and/or the product of formula (I) go into a complex comprising sulphur dioxide and hydrogen chloride, so the compounds (I) and (II) remain in solution and $SO_2$ and HCl are not released as gases. The complexing of amines with $SO_2$ in organic solvents is known in the literature (see for example J. Grundnes, S. D. Christian, J. Am. Chem. Soc. (1968) 90, 2239–2245), the teachings of which are incorporated by reference, while the—hypothetical—complexing with HCl has not previously been observed.

Irrespective of whether the hypothesis of complexing applies, the surprising circumstance whereby the reactants of the reaction remain in a homogeneous solution has proven to be advantageous with respect to yield and reaction. A further advantage is that it is possible to separate the desired reaction product from the solubilizer and the further reaction components and as the solubilizer, preferably toluene, is distilled off, preferably under vacuum; the sulphur dioxide that has formed and the hydrogen chloride are also removed in the process.

It is also advantageous to achieve separation of the product (I) by cooling the reaction mixture to a temperature below ambient temperature, preferably to 0 to 10° C., in particular to about 2 to 4° C., which leads to precipitation of the crude product. Subsequent treatment in a drying cabinet at elevated temperatures of preferably 35 to 75° C., in particular 40° C., and preferably under vacuum, in particular at a pressure of 1 to 300 mbar, preferably 50 to 180 mbar, most particularly preferably 50 to 150 mbar, yields the pure product, preferably as hydrochloride.

It is particularly preferred to carry out the process according to the invention with the stereoisomers of compound (II) which have the configuration (IIa) and/or (IIb):

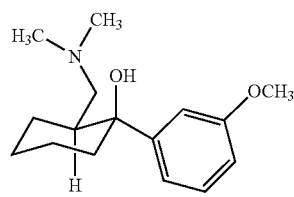

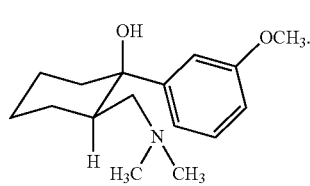

The reaction according to the invention with thionyl chloride leads, as expected with retention of the stereochemistry at the center of the reaction, to the corresponding stereoisomers of compound (I). It is also preferred to use the compound (II) in the process according to the invention as the enantiomer with the absolute configuration (IIa), i.e. as (1S,2S)-2-dimethylaminomethyl-1-(3-methoxyphenyl)-cyclohexanol, in particular as the hydrochloride. (1 S,2S)-[2-chloro-2-(3-methoxyphenyl)-cyclohexylmethyl]-dimethylamine, in particular in the form of the HCl salt, is obtained as the product here.

As known from EP 753 506 A1, the compounds of formula (I) have an analgesic effect and can be used as intermediate compounds to produce further analgesically active cyclohexyl compounds.

It is therefore also preferred to convert a compound of formula (I), produced by the process according to the invention by (d) catalytic hydrogenation, into a compound of formula (III):

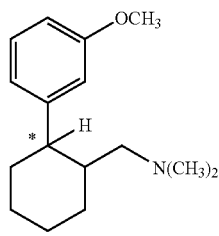

III

Hydrogenation is preferably carried out by heterogeneous catalysis with palladium on activated carbon, of which the quantity can be varied within a wide range between 1% through 5% to 10% palladium on activated carbon. Suitable solvents include alkyl alcohols, in particular methanol and ethanol. The compound (I) is conventionally used as the hydrochloride.

The hydrogenation step (d) is preferably carried out with retention of the stereochemistry on the carbon atom marked by an asterisk (*) in formula (I) or (III). The optionally formed quantity of compound (III) with inverted stereochemistry on the carbon*atom is so low that it can easily be separated during conventional working up. This process is therefore eminently suitable, starting from the enantiomer with the absolute configuration (IIa), via the corresponding enantiomer of compound (Ia)

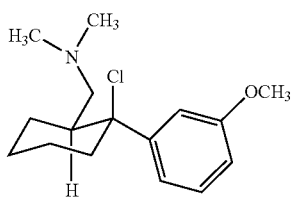

Ia for producing the compound (III) as the enantiomer with the absolute configuration (IIIa)

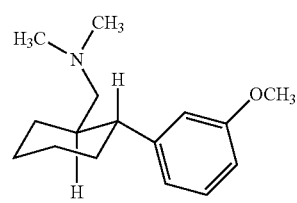

IIIa (The compound (IIIb) mirror-inverted to (IIa) can be correspondingly produced, starting from the optical antipode (IIb) via (Ib)).

As an alternative to hydrogenation by means of heterogeneous catalysis, the compound of formula (III) is also accessible by hydrogenation with complex zinc-boron hydrides of (I), as described in EP 0 753 506 A1.

The compound of formula (III), preferably produced by the process according to the invention, can also be converted by methyl ether cleavage in a further step (e) into the compound of formula (IV):

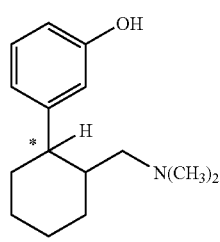

IV

Aqueous hydrobromic acid was formerly used for this methyl ether cleavage (EP 0 753 506 A1). However, these reaction conditions have various drawbacks. To achieve satisfactory yields therefore a high excess of acid has to be used, and, after the reaction has taken place, has to be laboriously distilled off and destroyed. The fact that methyl bromide is formed as the reaction product when HBr is used is particularly serious. Methyl bromide is a toxic, highly flammable gas with a boiling point of 4° C., which, it is suspected, damages the ozone layer of the earth's atmosphere and for which a production ban in the European Union is therefore being considered.

A process is therefore required which allows the desired methyl ether cleavage while avoiding the use of HBr and at the same time guarantees high yields of the product (IV).

It has accordingly been found that due to the simultaneous use of methionine and methane sulphonic acid, the methyl ether cleavage of (III) to (IV) can be carried out extremely easily and with high yields of more than 70%. (The use of methionine/methane sulphonic acid to produce phenols has been described by N. Fujii et al., J. Chem. Soc. Perkin I (1977) 2288–2298, but they do not convert any amine-substituted compounds). Here the compound (III), preferably in the form of the hydrochloride, is suspended in a mixture of a large excess of methane sulphonic acid, conventionally between 5 and 40 equivalents, in particular 10 to 30 equivalents, particularly preferably about 20 equivalents, and 1 to 2, equivalents preferably about 1.1 to 1.3 equivalents of methionine, and then heated for 1 to 12 hours, preferably 3 to 8 hours, in particular 5 hours, to temperatures of 50 to 100° C., preferably 70 to 90° C. After cooling and conventional working up, the desired phenol (IV) is obtained in high yields without by-products and at most very small quantities of unreacted starting material (III), preferably as hydrochloride; by recrystallisation from water, (IV) is obtained in the form of hydrochloride hydrates. It is surprising in this connection that the dimethylamino group otherwise very unstable in an acid medium proves to be stable compared with the large excess of methane sulphonic acid present.

An efficient process for producing the analgesic compound known from EP 0 753 506 A1 with the absolute configuration (IVa), starting from the tertiary alcohol (II) with the absolute configuration (IIa), is thus provided which can also be carried out on an industrial scale. The synthesis sequence is shown in diagram I. (The same applies to the optical antipode of (IVa) with (1S,2S) configuration.

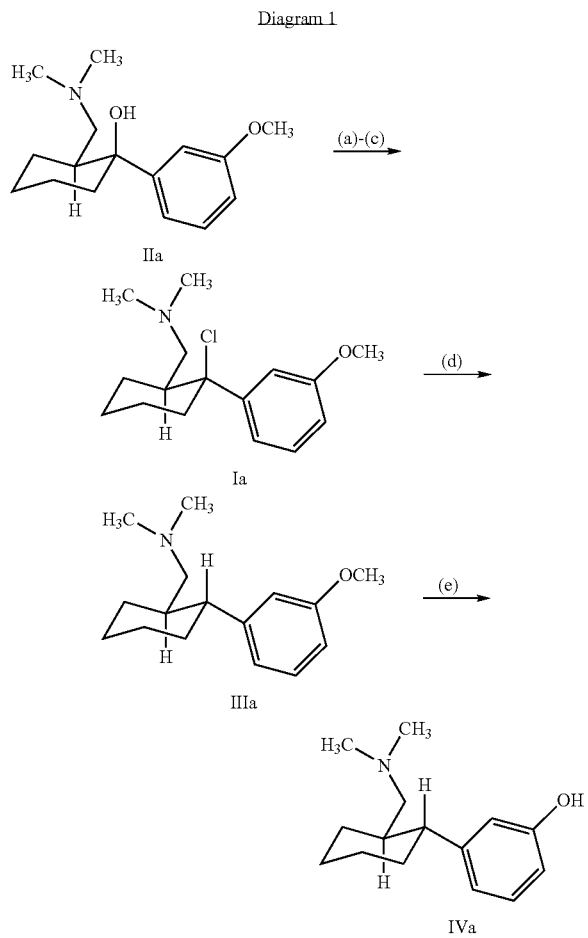

The invention will be described hereinafter by examples, without being limited thereto.

EXAMPLES

The syntheses were carried out using commercially available reagents and substances or with compounds that had been produced by processes known from the literature.

The reaction products were identified and the chemical and optical purity analysed by NMR spectroscopy and HPLC chromatography.

Example 1

Chlorination Using Thionyl Chloride: Production of (1S,2S)-[2-chloro-2-(3-methoxy-phenyl)-cyclohexylmethyl]-dimethylamine hydrochloride 3 kg (10 mol) (1S,2S)-2-dimethylaminomethyl-1-(3-methoxy-phenyl)-cyclohexanol hydrochloride were suspended in 10 l toluene and heated to 30° C. 1.9 kg (16 mol) thionyl chloride were added within 10 min. The mixture was heated to 35° to 45° C. A clear solution was produced after 2 to 3 hours. Further processing was effected according to variant A or B.

Variant A:

3 kg toluene were distilled off under vacuum via a gas washer. Hydrogen chloride gas and sulphur dioxide escaped as the toluene was distilled off. The mixture was then cooled to 2° C. and stirred for 2 hours at this temperature. The precipitate was centrifuged off and thoroughly rewashed with toluene. The product could be used directly or after drying for subsequent hydrogenation. The yield was 2.87 kg (90% of theoretical) (1S,2S)-[2-chloro-2-(3-methoxyphenyl)-cyclohexylmethyl]-dimethylamine hydrochloride.

Variant B:

The reaction mixture was cooled to 2° C. and stirred for 4 hours. The precipitate formed was centrifuged off and dried in a drying cabinet for 17 hours at 40° C. and under a vacuum of <150 mbar. The product thus obtained could be used for subsequent hydrogenation. The yield was 2.55 kg (80% of theoretical) (1S,2S)-[2-chloro-2-(3-methoxy-phenyl)-cyclohexylmethyl]-dimethylamine hydrochloride.

Identification was effected by comparing the analytical data of the product obtained in variant A or B and the compound known from EP 0 753 506 A1, which exhibited identity. The chemical and optical purity was analysed by HPLC on a Nucleosil 100-5 C8 HD column (250×3 mm) by gradient elution with acetonitrile/water. Detection was effected using a UV spectrometer at 210 nm.

Example 2

Heterogeneously Catalysed Hydrogenation: Hydrogenation of (1S,2S)-[2-chloro-2-(3-methoxy-phenyl)-cyclohexylmethyl]-dimethylamine hydrochloride 3.18 kg (10 mol) (1S,2S)-[2-chloro-2-(3-methoxy-phenyl)-cyclohexylmethyl] dimethylamine hydrochloride (from Example 1) were dissolved in 15 l methanol, and 350 g palladium on activated carbon 5% were added. Hydrogen was introduced at normal pressure and ambient temperature until hydrogenation was complete. The catalyst was suction filtered, the solvent concentrated to a small volume and the base liberated using aqueous sodium hydroxide solution. After shaking out the aqueous phase using ethyl acetate and distilling off the organic solvent 2.47 kg (100% of theoretical) (1R,2R)-[2-(3-methoxyphenyl)-cyclohexylmethylamine]-dimethylamine as a slightly yellow colored oil remained.

The oil was dissolved in acetone and the hydrochloride precipitated using hydrochloric acid gas. 2.27 kg (80% of theoretical) (1R,2R)-[2-(3-methoxy-phenyl)-cyclohexylmethyl]-dimethylamine hydrochloride were obtained as a col orless powder with a content of <10% of (1R,2S)-[2-(3-methoxy-phenyl)-cyclohexylmethyl]-dimethylamine hydrochloride, which was removed from 2-propanol by recrystallisation.

Identification was effected by comparing the analytical data of the product obtained and the compound known from EP 0 753 506 A1, which exhibited identity. The chemical and optical purity was analysed by HPLC on a Nucleosil 100-5 C8 HD column (250×3 mm) by gradient elution with acetonitrile/water. Detection was effected using a UV spectrometer at 210 nm.

Example 3

Methylether Cleavage Using Methane Sulphonic Acid/Methionine: Production of (1R,2R)-3-(2-dimethylaminomethyl-cyclohexyl)-phenol hydrochloride 2.83 kg (10 mol) (1R,2R)-[2-(3-methoxyphenyl)-cyclohexyl-methyl]-dimethylamine hydrochloride were suspended in a mixture of 8.70 l methane sulphonic acid and 1.50 kg (D,L) methionine and heated for 5 hours to 70° to 90° C. The mixture was cooled to 30° C. and adjusted using 32% aqueous sodium hydroxide solution to a pH of 12 to 14. The base was extracted with ethyl acetate. After concentrating the organic solvent and precipitation in acetone with hydrochloric acid gas (or aqueous hydrochloric acid) 1.86 kg (80%) (1R,2R)-3-(2-dimethylaminomethyl-cyclohexyl)-phenol hydrochloride with a content of <1% of the starting product (1R,2R)-[2-(methoxyphenyl)-cyclohexyl-methyl]-dimethylamine hydrochloride.

Recrystallisation from water produced colorless crystals (1.5 kg, 80%) of (1R,2R)-3-(2-dimethylaminomethyl-cyclohexyl)-phenol hydrochloride dihydrate.

Identification was effected by comparing the analytical data of the product obtained and the compound known from EP 0 753 506 A1, which exhibited identity. The chemical and optical purity was analysed by HPLC on a Nucleosil 100-5 C8 HD column (250×3 mm) by gradient elution with acetonitrile/water. Detection was effected using a UV spectrometer at 210 nm.

What is claimed is:

1. A process for producing a compound corresponding to formula (I)

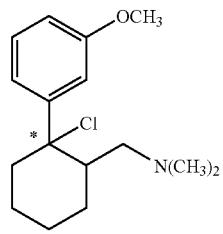

I in the form of its racemates, its pure stereoisomers, or in the form of mixtures of stereoisomers, in any mixing ratio; in the illustrated form or in the form of its salts, or in the form of its solvates; comprising the steps of:

(a) suspending a compound corresponding to formula (II)

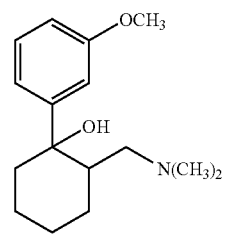

II in a solvent selected from the group consisting of toluene, o-xylene, m-xylene, p-xylene and mixtures thereof, wherein said compound corresponding to formula (II) is present in the form of its racemates, its pure stereoisomers, its enantiomers or diastereomers, or in the form of mixtures of stereoisomers, in any mixing ratio; in the illustrated form or in the form of its salts, or in the form of its solvates;

(b) adding thionyl chloride to the resultant suspension to form a reaction mixture and (c) separating the reaction product comprising the tertiary Cl group of formula (I) from the reaction mixture.

2. A process according to claim 1, wherein said compound corresponding to formula (I) is produced in the form of an enantiomer or a diastereomer or a mixture thereof.

3. A process according to claim 1, wherein said compound corresponding to formula (I) is produced in the form of its physiologically acceptable salts.

4. A process according to claim 1, wherein said compound corresponding to formula (I) is produced in the form of a hydrochloride.

5. A process according to claim 1, wherein said compound corresponding to formula (I) is produced in the form of a hydrate.

6. A process according to claim 1, wherein the step of separating the reaction product of formula (I) involves distillation of the reaction mixture.

7. A process according to claim 1, wherein the step of separating the reaction product of formula (I) involves precipitating the reaction product of formula (I) by cooling the reaction mixture to below ambient temperature and then drying the reaction product at temperatures between 35° C. and 75° C.

8. A process according to claim 7, wherein the drying step is performed under vacuum.

9. A process according to claim 1, wherein the solvent is toluene.

10. A process according to claim 1, wherein 1 to 2 equivalents of thionyl chloride, based on the amount of the compound of formula (II), are added.

11. A process according to claim 10, wherein 1.5 to 1.7 equivalents of thionyl chloride, based on the amount of the compound of formula (II), are added.

12. A process according to claim 10, wherein 1.6 equivalents of thionyl chloride, based on the amount of the compound of formula (II), are added.

13. A process according to claim 1, wherein a reaction is carried out with thionyl chloride at a temperature of 30 to 50° C.

14. A process according to claim 1, wherein a reaction is carried out with thionyl chloride at a temperature of 35 to 45° C.

15. A process according to claim 1, wherein a reaction is carried out with thionyl chloride for 1 to 4 hours.

16. A process according to claim 1, wherein a reaction is carried out with thionyl chloride for 2 to 3 hours.

17. A process according to claim 1, wherein said compound corresponding to formula (II) is a compound corresponding to formula (IIa) or (IIb):

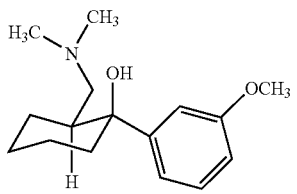
IIa

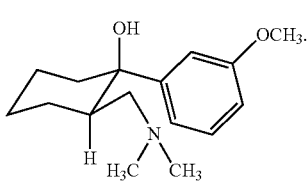
IIb

18. A process according to claim 1, wherein said compound corresponding to formula (II) is present as a mixture of compounds corresponding to formula (IIa) and (IIb):

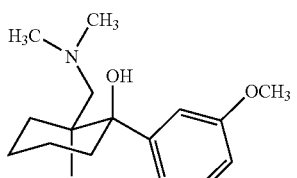
IIa

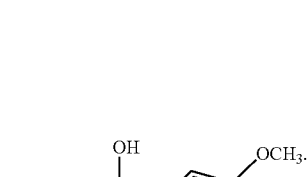
IIb

19. A process according to claim 1, wherein said compound corresponding to formula (II) is a enantiomer corresponding to formula (IIa):

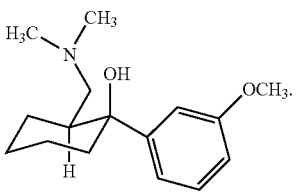
IIa

20. A process according to claim 1, for producing a compound corresponding to formula (III)

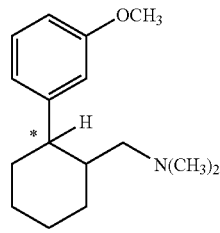
III comprising the step of
(d) subjecting the compound corresponding to formula (I) to catalytic hydrogenation with palladium on activated carbon as a catalyst.

21. A process according to claim 20, wherein in the hydrogenation (d) is carried out while retaining the stereochemistry on the carbon atom marked by an asterisk (*) in formula (I) or formula (III).

22. A process according to claim 20, for producing a compound corresponding to formula (IV)

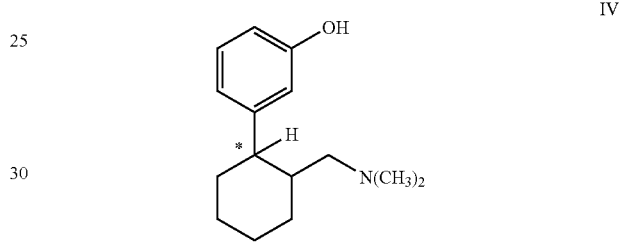
IV comprising the step of
(e) subjecting the compound corresponding to formula (III) to methyl ether cleavage with methionine sulphonic acid or methane sulphonic acid or a mixture thereof.

23. A process according to claim 22, wherein said compound corresponding to formula (II) is a compound corresponding to formula (IIa),

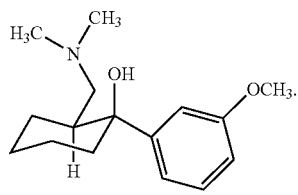
IIa and said process steps (a) to (e) are performed to produce a compound corresponding to formula (IVa)

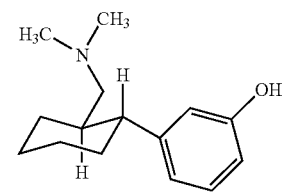
IVa in the form of its hydrochloride or its hydrochloride hydrate or a combination thereof.

* * * * *